United States Patent [19]

Miwa et al.

[11] Patent Number: 4,605,799

[45] Date of Patent: Aug. 12, 1986

[54] PROCESS FOR SEPARATING A HALOGENATED TOLUENE ISOMER

[75] Inventors: Kishio Miwa; Kuniyuki Tada, both of Kamakura; Takehisa Inoue, Tokyo, all of Japan

[73] Assignee: Toray Industries, Inc., Tokyo, Japan

[21] Appl. No.: 288,132

[22] Filed: Jul. 29, 1981

[30] Foreign Application Priority Data

Aug. 13, 1980 [JP] Japan ................................. 55-110395
Nov. 27, 1980 [JP] Japan ................................. 55-165821

[51] Int. Cl.$^4$ ............................................. C07C 17/38
[52] U.S. Cl. ................................................... 570/211
[58] Field of Search ........................................ 570/211

[56] References Cited

U.S. PATENT DOCUMENTS

| | | | |
|---|---|---|---|
| 2,958,708 | 11/1960 | Fleck et al. | 570/211 |
| 3,700,744 | 10/1972 | Berger et al. | 585/805 |
| 4,254,062 | 3/1981 | Wambach et al. | 570/211 |

*Primary Examiner*—Charles F. Warren
*Assistant Examiner*—Joseph A. Boska
*Attorney, Agent, or Firm*—Scully, Scott, Murphy & Presser

[57] ABSTRACT

Provided is a process for separating a halogenated toluene isomer from a feed containing a mixture of halogenated toluene isomers by adsorptive separation techniques using a Y type zeolite as an adsorbent and an alkyl aromatic hydrocarbon, 3,4-dihalotoluene or 4-haloorthoxylene as a desorbent.

8 Claims, No Drawings

PROCESS FOR SEPARATING A HALOGENATED TOLUENE ISOMER

BACKGROUND OF THE INVENTION

This invention relates to a process for separating a halogenated toluene isomer and more particularly to the improvement of a process for separating a halogenated toluene isomer from a feed containing a mixture of halogenated toluene isomers by adsorptive separation techniques using an adsorbent and a desorbent.

It is known from Japanese Patent Publication No. 5155/1962 that a halogenated toluene isomer is adsorptively separated with X type zeolite. In this prior art publication there is used chlorobenzene as a desorbent. However, a satisfactory effect of adsorptive separation is not obtainable from known combinations of adsorbents and desorbents.

SUMMARY OF THE INVENTION

It is an object of this invention to provide a combination of an adsorbent and a desorbent capable of being used effectively when selectively adsorbing a halogenated toluene isomer from a feed containing a mixture of halogenated toluene isomers by using a solid adsorbent.

It is another object of this invention to provide a combination of an adsorbent and a desorbent which combination exhibits a remarkable effect in the separation and recovery of a halogenated toluene isomer from a mixture of halogenated toluene isomers continuously while repeating adsorption and desorption steps alternately.

Other objects and advantages of this invention will become apparent from the following description.

The foregoing objects of this invention can be attained by using as an adsorbent a Y type zeolite and a desorbent containing at least one member selected from the group consisting of alkyl aromatic hydrocarbons, 3,4-halotoluene and 4-haloorthoxylene in the selective adsorptive separation of a halogenated toluene isomer from a feed containing a mixture of halogenated toluene isomers.

DETAILED DESCRIPTION OF THE INVENTION

Fundamental operations for separating a halogenated toluene isomer from a mixture of halogenated toluene isomers by continuous adsorptive separation techniques comprise the following adsorption and desorption steps.

(1) In the adsorption step, a feed containing a mixture of halogenated toluene isomers is contacted with an adsorbent which has been subjected to the desorption step as will be referred to in (2) below, whereby a more selectively adsorbed component in the feed is selectively adsorbed while displacing a part of the desorbent which remains in the adsorbent. At the same time, a less selectively adsorbed component in the feed is recovered as a raffinate stream together with the desorbent.

(2) In the desorption step, the selectively adsorbed component is displaced from the adsorbent by the desorbent and is recovered as an extract stream.

The adsorbent used in the above adsorptive separation process is required to have the capability of adsorbing the more selectively adsorbed component more selectively than the other halogenated toluene isomer(s) in the mixture. On the other hand, the desorbent used in the above adsorptive separation process should have the function of displacing the selectively adsorbed component from the adsorbent in the desorption step, and it goes without saying that the desorbent itself must be displaced in the following adsorption step by the more selectively adsorbed component in the feed to allow the adsorbent to be used continuously in a recyclic manner. That is, a desorbent which is adsorbed more strongly than the more selectively adsorbed component is preferable in the desorption step, while a desorbent which is adsorbed more weakly than the more selectively adsorbed component is preferable in the adsorption step. For simultaneous satisfaction of such requirements contrary to each other, it is necessary to select a desorbent so that the adsorptive selectivity between the more selectively adsorbed component and the desorbent resemble each other.

In such an adsorptive separation process, moreover, the adsorbent which has been contacted with the desorbent for displacing the more selectively adsorbed component in the desorption step is recycled, as it contains the desorbent, to the adsorption step of (1) and is used for selective adsorption of the more selectively adsorbed component in the feed. Consequently, in the adsorption step there occurs a competitive adsorption between the more selectively adsorbed component and the desorbent remaining in the adsorbent.

Therefore, another important factor for the selection of a desorbent is that, since the selective adsorption of a halogenated toluene isomer is performed in the presence of the desorbent, the selective adsorption capability of an adsorbent for the more selectively adsorbed component in comparison with the other halogenated toluene isomer(s) must not be affected by the presence of the desorbent.

The selective adsorption capability of an adsorbent for the more selectively adsorbed component when compared with the other halogenated toluene isomer(s) and a desorbent, can be expressed in terms of a selectivity value, $\alpha(A/B \text{ or } D)$, of the more selectively adsorbed component represented by the following equation (a):

$$\alpha(A/B \text{ or } D) = \frac{(\text{wt. percent of } A \text{ in adsorbed phase}/ \text{wt. percent of } B \text{ or } D \text{ in adsorbed phase})}{(\text{wt. percent of } A \text{ in unadsorbed phase}/ \text{wt. percent of } B \text{ or } D \text{ in unadsorbed phase})} \quad (a)$$

wherein A is a more selectively adsorbed component, B is the other isomer(s) and D is a desorbent, with adsorbed phase and unadsorbed phase being in equilibrium.

As selectivity becomes greater than unity, there is preferential adsorption of the more selectively adsorbed component. That is, for the adsorbent, the larger the value of $\alpha(A/B)$, the better.

As selectivity approaches unity, there is no preferential adsorption of the more selectively adsorbed component, and in this case an attempt to recover the more selectively adsorbed component in high purity results in an increased concentration of the more selectively adsorbed component in the raffinate stream, that is, the recovery of the more selectively adsorbed component decreases. On the other hand, an attempt to improve the recovery of the more selectively adsorbed component would result in an increased concentration of the other isomer(s) in the extract stream, so that the recovered more selectively adsorbed component inevitably decreases in its purity.

The α(A/D) in the equation (a) represents an adsorptive selectivity between the more selectively adsorbed component and a desorbent. In order that the desorbent and the more selectively adsorbed component may be adsorbed almost equally, it is preferable that the α(A/D) take a value near unity, particularly in the range of from 0.5 to 2.0. If the α(A/D) value is far larger than unity, there will be required a large amount of desorbent for displacing the selectively adsorbed component from the adsorbent in the desorption step, or it will become no longer possible to displace most of the more selectively adsorbed component, thus resulting in a decreased recovery of the more selectively adsorbed component, which is uneconomical. Conversely, if the α(A/D) value is far smaller than unity, the desorbent will become difficult to be displaced by the more selectively adsorbed component in the feed in the adsorption step; as a result, the adsorption of the more selectively adsorbed component substantially decreases, and the concentration of the more selectively adsorbed component in the raffinate stream increases, thus causing a decrease in the recovery of the more selectively adsorbed component, which is also uneconomical.

Therefore, the adsorbent and the desorbent to be used in the adsorptive separation for a mixture of halogenated toluene isomers must be selected so as to satisfy the requirement that the α(A/B) value measured in the presence of the desorbent should be as large as possible and that the α(A/D) value should be close to unity. This is very important for making such an adsorptive separation process as the present invention more economical.

The halogenated toluene isomers mixture used in the process of this invention is a mono-halogen nuclear substitution product of toluene and it contains at least two kinds of isomers selected from o-, m- and p-halotoluene isomers. The halogen may be any of chlorine, bromine, iodine and fluorine. Particularly, the process of this invention is preferably used for the separation of chloro- or bromotoluene isomers.

The Y type zeolite used as an adsorbent in the process of this invention is a crystalline aluminosilicate belonging to faujasite type zeolites, and it can be expressed in terms of the following mole ratio of oxide (see U.S. Pat. No. 3,130,007):

$$0.9 \pm 0.2 M_{2/n}O:Al_2O_3:3\sim 6SiO_2:yH_2O$$

M: cation
n: valence of M
y: differs according to the degree of hydration

The M is an optional cation, but usually available are Y type zeolites wherein M is sodium. In this case, it is necessary that sodium be ion-exchanged with at least one cation selected from Group IA and IIA metals and proton. Known ion-exchange methods may be adopted. Usually, the ion-exchange can be performed easily by treating the aforesaid sodium-containing Y type zeolite with an aqueous solution containing the above cations. Particularly, the ion-exchange with potassium ion using an aqueous solution of potassium nitrate or chloride or the like is preferred. In this case, the exchange ratio of the Y type zeolite with potassium ion is preferably not less than 50%, more preferably not less than 70%, of the cation before ion-exchange.

The Y type zeolite used in the process of this invention may contain other cationic components than potassium ion; for example, those containing Group IA, IIA, IIIA and IVA metals other than sodium or proton are used preferably. Particularly preferred cations are strontium, barium, yttrium, rubidium and proton. These cations other than potassium may be used alone or in combination and usually they are used together with potassium in such a quantitative relation that the remaining sodium is not more than 10%.

The desorbent used in the process of this invention contains as an essential component an alkyl aromatic hydrocarbon, 3,4-dihalotoluene, or 4-haloorthoxylene.

The alkyl aromatic hydrocarbon as referred to herein indicates a monocyclic alkyl aromatic hydrocarbon with one to four $C_1$-$C_3$ alkyl groups substituted onto the benzene ring. Preferred examples are toluene, ethylbenzene, m-xylene, o-xylene, m-diethylbenzene, o-diethylbenzene, and p-diisopropylbenzene.

The halogen in 3,4-dihalotoluene and 4-haloorthoxylene may be chlorine, bromine, iodine or fluorine, but it is preferred to select a compound having the same halogen as that in the halogenated toluene to be separated by adsorption.

The above components of the desorbent used in the process of this invention may be used alone or in combination, or may be used together with a diluent such as paraffin or a cycloparaffinic hydrocarbon.

Operational conditions for the adsorptive separation process of this invention involve temperatures ranging from 0° to 350° C., particularly preferably from room temperature to 250° C., and pressures ranging from atmospheric pressure to 40 kg/cm², particularly preferably from nearly atmospheric pressure to 30 kg/cm². The adsorptive separation process of this invention is applicable in both vapor phase and liquid phase, but the latter is preferable in order to reduce undesirable side reactions of the feed or desorbent while keeping the operating temperature.

Working examples of this invention will be given hereinunder to further illustrate the process of the invention.

EXAMPLE 1

NaY type zeolite powder ("SK-40", a product of Union Carbide Corp.) was mixed with alumina sol as a binder in an amount of 10% by weight in terms of Al$_2$O$_3$, then the mixture was subjected to extrusion molding to obtain granules of 24 to 32 mesh, which were dried at 100° C., then calcined at 500° C. for 1 hour and treated with an aqueous potassium nitrate solution to prepare a Y type adsorbent containing potassium ion (90% exchange ratio).

Then, in order to check the adsorbent for its selectivity value among chlorotoluene (CT) isomers, 2 g. of the adsorbent which had been calcined at 500° C. for 1 hour and 2 g. of a liquid-phase mixture consisting of a CT isomers mixture, a desorbent and n-nonane were charged into an autoclave having a content volume of 5 ml., then allowed to stand for 1 hour at 130° C. while stirring was applied at times. The desorbent used was chlorobenzene (CB). The composition of the fed liquid-phase mixture was n-nonane:P-CT:m-CT:o-CT:CB:1:1:1:1:3 (in weight ratio). The n-nonane was added as a standard substance in gas chromatography, and it is a substantially inert substance under the above-mentioned experimental conditions. The composition of the liquid-phase mixture after contact with the adsorbent was analyzed by gas chromatography, and selectivity values for the CT isomers and the desorbent were determined using the equation (1), the results of which are set out in Table 1.

EXAMPLE 2

Y type zeolite granules were prepared in the same manner as in Example 1, which were then treated with various aqueous nitrate solutions in addition to the treatment with aqueous potassium nitrate solution applied in Example 1 to prepare Y type adsorbents containing potassium ion and other cations.

Then, selectivity values of these adsorbents for chlorotoluene were determined in the same way as in Example 1, the results of which are shown in Table 1.

TABLE 1

| Cation | $\alpha$p-CT/m-CT | $\alpha$p-CT/o-CT | $\alpha$p-CT/D |
|---|---|---|---|
| K$^+$ | 1.71 | 1.53 | 1.13 |
| 0.1Sr$^{++}$ + 0.8K$^+$ | 1.79 | 1.64 | 1.23 |
| 0.1Rb$^+$ + 0.9K$^+$ | 1.82 | 1.60 | 1.17 |
| 0.1H$^+$ + 0.9K$^+$ | 1.98 | 1.72 | 1.32 |
| 0.05Y$^{+++}$ + 0.85K$^+$ | 1.76 | 1.63 | 1.26 |

COMPARATIVE EXAMPLE 1

In Example 1 there was used an X type zeolite as the adsorbent, the results of which are shown in Table 2.

TABLE 2

| Cation | $\alpha$p-CT/m-CT | $\alpha$p-CT/o-CT | $\alpha$p-CT/D |
|---|---|---|---|
| Na$^+$ | 1.04 | 0.80 | 0.78 |

EXAMPLE 3

Y type zeolite granules were prepared in the same manner as in Example 1, which were then cation-exchanged thoroughly with an aqueous potassium nitrate solution to prepare a K-Y type adsorbent (90% exchange ratio).

Selectivity value of this adsorbent between bromotoluene (BT) isomers was determined in the same way as in Example 1, provided the composition of the feed used herein was n-nonane:p-BT:m-BT:CB=1:1:1:3. The results are shown in Table 3.

TABLE 3

| Adsorbent | $\alpha$p-BT/m-BT | $\alpha$p-BT/D |
|---|---|---|
| K-Y | 2.1 | 1.7 |

EXAMPLE 4

Sodium Y type zeolite granules were subjected to ion-exchange treatment using potassium nitrate so that not less than 90% of the sodium ions were ion-exchanged with potassium, then dried at 120° C. for 5 hours and calcined at 500° C. for 1 hour to prepare a K-Y type adsorbent.

Then, 1.8 g. of the adsorbent and 2.5 g. of a liquid-phase mixture consisting of a chlorotoluene (CT) isomers mixture, an alkyl aromatic hydrocarbon and n-nonane were charged into an autoclave having a content volume of 5 ml., then allowed to stand for about 1 hour at 130° C. while stirring was applied at times.

The composition of the fed liquid-phase mixture was n-nonane:o-CT:m-CT:p-CT:alkyl aromatic hydrocarbon=1:1:1:1:4 (in weight ratio). The n-nonane was added as a standard substance in gas chromatography, and it is substantially inet to the adsorbent under the above-mentioned conditions.

The composition of the liquid-phase mixture after contact with the adsorbent was analyzed by gas chromatography, and selectivity values were calculated on the basis of variation in the composition of the liquid-phase mixture, the results of which are set out in Table 4.

TABLE 4

| Desorbent | $\alpha$p-CT/m-CT | $\alpha$p-CT/o-CT | $\alpha$p-CT/D |
|---|---|---|---|
| Toluene | 2.11 | 1.85 | 1.01 |
| Ethylbenzene | 1.83 | 1.64 | 0.85 |
| m-Xylene | 1.89 | 1.68 | 1.86 |

COMPARATIVE EXAMPLE 2

Selectivity values are shown in Table 5 with respect to each of the case where no desorbent was used in Example 4 and the case where chlorobenzene was used as a desorbent therein.

TABLE 5

| Desorbent | $\alpha$p-CT/m-CT | $\alpha$p-CT/o-CT | $\alpha$p-CT/D |
|---|---|---|---|
| None | 1.79 | 1.62 | — |
| Chlorobenzene | 1.71 | 1.53 | 1.13 |

EXAMPLE 5

In Example 4 a mixture of n-nonane:o-CT:p-CT:alkyl aromatic hydrocarbon=1:1:1:3 was used as the feed. Selectivity values determined are shown in Table 6.

TABLE 6

| Desorbent | $\alpha$p-CT/o-CT | $\alpha$p-CT/D |
|---|---|---|
| m-Diethylbenzene | 2.11 | 1.20 |
| p-Diisopropylbenzene | 3.21 | 1.58 |

EXAMPLE 6

In Example 4 a part of the potassium ions of the K-Y type adsorbent was substituted by proton, zirconium and strontium, and toluene was used as the desorbent, under which conditions there were determined selectivity values as shown in Table 7.

TABLE 7

| Cation | $\alpha$p-CT/m-CT | $\alpha$p-CT/o-CT | $\alpha$p-CT/D |
|---|---|---|---|
| 0.1H$^+$ + 0.9K$^+$ | 2.01 | 1.79 | 0.79 |
| 0.05ZrO$^{++}$ + 0.05H$^+$ + 0.85K$^+$ | 2.27 | 1.87 | 0.89 |
| 0.1Sr$^{++}$ + 0.8K$^+$ | 1.95 | 1.83 | 0.85 |

EXAMPLE 7

In Example 4 a mixture of n-nonane m-bromotoluene (m-BT):p-bromotoluene (p-BT):ethylbenzene=1:1:1:3 was used as the feed. Selectivity values determined are shown in Table 8.

COMPARATIVE EXAMPLE 3

Selectivity values are shown also in Table 8 with respect to each of the case where chlorobenzene was used in place of the alkyl aromatic hydrocarbon in Example 7 and the case where no desorbent was used therein.

TABLE 8

| Desorbent | αp-BT/m-BT | αp-BT/D |
| --- | --- | --- |
| Ethylbenzene | 2.30 | 1.52 |
| Chlorobenzene | 2.08 | 1.89 |
| None | 2.26 | — |

EXAMPLE 8

Sodium Y type zeolite granules were subjected to ion-exchange treatment using potassium nitrate so that not less than 90% of the sodium ions were ion-exchanged with potassium, then dried at 120° C. for 5 hours and calcined at 500° C. for 1 hour to prepare a K-Y type adsorbent.

Then, 1.8 g. of the adsorbent and 2.5 g. of a liquid-phase mixture consisting of a chlorotoluene (CT) isomers mixture, 3,4-dichlorotoluene or 4-chloroorthoxylene and n-nonane were charged into an autoclave having a content volume of 5 ml., then allowed to stand for about 1 hour at 130° C. while stirring was applied at times.

The composition of the fed liquid-phase mixture was n-nonane:o-CT:m-CT:p-CT:3,4-dichlorotoluene or 4-chloroorthoxylene=1:1:1:1:4 (in weight ratio). The n-nonane was added as a standard substance in gas chromatography, and it is substantially inert to the adsorbent under the above-mentioned conditions.

The composition of the liquid-phase mixture after contact with the adsorbent was analyzed by gas chromatography, and selectivity values were calculated on the basis of variation in the composition of the liquid-phase mixtue, the results of which are shown in Table 9.

TABLE 9

| Desorbent | αp-CT/m-CT | αp-CT/o-CT | αp-CT/D |
| --- | --- | --- | --- |
| 3,4-Dichlorotoluene | 1.96 | 1.82 | 1.40 |
| 4-Chloroorthoxylene | 1.89 | 1.80 | 1.32 |

EXAMPLE 9

In Example 8 a part of the potassium ions of the K-Y type adsorbent was substituted by proton, zirconium and magnesium, and 3,4-dihalotoluene or 4-haloorthoxylene was used as the desorbent, under which condition there were determined selectivity values as shown in Table 10.

TABLE 10

| Adsorbent Cation | Desorbent | αp-CT/m-CT | αp-CT/o-CT | αp-CT/D |
| --- | --- | --- | --- | --- |
| $0.1H^+ + 0.9K^+$ | 4-chloro-orthoxylene | 2.04 | 1.87 | 1.40 |
| $0.05ZrO^{++} + 0.05H^+ + 0.85K^+$ | 4-chloro-orthoxylene | 2.23 | 1.99 | 1.48 |
| | 3,4-dichlorotoluene | 2.14 | 1.91 | 1.42 |
| $0.1Mg^{++} + 0.8K^+$ | 3,4-dichlorotoluene | 1.97 | 1.81 | 1.33 |

What is claimed is:

1. In an adsorptive-separation process for recovering the p-isomer from a mixture of monohalogenated toluene isomers containing the p-isomer and at least one other isomer, the improvement characterized by using as an adsorbent a Y type zeolite containing potassium ion and a desorbent containing at least one member selected from the group consisting of 3,4-dihalotoluene, 4-haloorthoxylene and a monocyclic alkyl aromatic hydrocarbon with one to four $C_1$-$C_3$ alkyl groups substituted onto the benzene ring whereby the p-isomer is selectively adsorbed and separated from said mixture.

2. The process as defined in claim 1, in which said alkyl aromatic hydrocarbon is toluene.

3. The process as defined in claim 1, in which said 3,4-dihalotoluene is 3,4-dichlorotoluene.

4. The process as defined in claim 1, in which said 4-haloorthoxylene is 4-chloroorthoxylene.

5. The process as defined in claim 1, in which said monohalogenated toluene is chlorotoluene.

6. The process as defined in claim 1, in which said process is carried out at a temperature in the range of from 0° to 350° C. and at a pressure in the range of from atmospheric pressure to 40 kg/cm².

7. The process as defined in claim 1, in which said process is carried out at a temperature in the range of from room temperature to 250° C. and at a pressure in the range of from atmospheric pressure to 30 kg/cm².

8. The process as defined in claim 1, in which said alkyl aromatic hydrocarbon is ethylbenzene, m-xylene, o-xylene, m-diethylbenzene, o-diethylbenzene or p-diisopropylbenzene.

* * * * *